United States Patent [19]
Caulfield et al.

[11] Patent Number: 5,692,640
[45] Date of Patent: Dec. 2, 1997

[54] SYRINGE CONTENT IDENTIFICATION SYSTEM

[76] Inventors: Patricia E. Caulfield; Arthur E. Caulfield, both of 7 Ministerial Dr., Merrimack, N.H. 03054

[21] Appl. No.: 567,568

[22] Filed: Dec. 5, 1995

[51] Int. Cl.⁶ .................................................. G07F 11/68
[52] U.S. Cl. .................. 221/70; 221/73; 221/199; 221/282; 604/189
[58] Field of Search ............... 221/70, 73, 199, 221/282; 604/189

[56] References Cited

U.S. PATENT DOCUMENTS

| | | | |
|---|---|---|---|
| 3,391,694 | 7/1968 | Spaeth | 128/218 |
| 3,698,383 | 10/1972 | Baucom | 128/26 |
| 4,772,355 | 9/1988 | Leahy | 221/73 |
| 4,781,696 | 11/1988 | Moulding, Jr. et al. | 604/189 |
| 4,857,716 | 8/1989 | Gombrich et al. | 235/462 |
| 4,865,549 | 9/1989 | Sonsteby | 434/262 |
| 4,921,277 | 5/1990 | McDonough | 283/81 |
| 4,976,351 | 12/1990 | Mangini et al. | 206/232 |
| 5,048,870 | 9/1991 | Mangini et al. | 283/81 |
| 5,397,017 | 3/1995 | Muza et al. | 221/199 |
| 5,443,178 | 8/1995 | Holmes | 221/70 |

*Primary Examiner*—William E. Terrell
*Assistant Examiner*—Khoi H. Tran

[57] ABSTRACT

A system for establishing and maintaining the identity of a medication in a syringe (80) from the point in time that a medication is withdrawn from a vial (30) to the point in time that the medication is administered to a patient. This method is based on integrating a label dispenser (40) including preprinted, pressure sensitive, syringe labels (71) with a medicine vial (30). As the medication is withdrawn from the vial a label is provided that identifies the contents of the vial. When this label is applied to the syringe it provides the ability to verify that the correct medication and dosage is being administered to the correct patient. Subsequently the label can be removed from the syringe and used to provide a permanent record of the administration.

10 Claims, 6 Drawing Sheets

Awondacook County Pediatric Association
104 Sambedia Drive
Pearls Falls, Maine, 04569
(207) 824-5654

Immunization Record of  John Doe, III          Date of Birth 7/3/95

| Vaccine | Manufacturer | Lot # | Site Given | Given by | Date | Parent or Guardian |
|---|---|---|---|---|---|---|
| DTP,DTP-Hib,DT-#1 | Lederle | 990-89 | ⑬ AL thigh | S Jones RN | 9/4/95 | John Doe II |
| DTP,DTP-Hib,DT-#2 | DTP 0.5 mL 1 of 10 Marsh-Laval Labs TRIVALSOL Lot 840-499 Expires Dec 98 | | ⑭ AL thigh | S Jones RN | 11/2/95 | John Doe II |
| DTP,DTP-Hib,DT-#3 | | | | | | |
| DTP,DTP-Hib,DT-#4 | | | | | | |
| DTaP,DTP,DT- #5 | | | | | | |
| OPV or IPV #1 | | | | | | |
| OPV or IPV #2 | | | | | | |

SYRINGE CONTENT IDENTIFICATION SYSTEM

BACKGROUND

1. Field of the Invention

This invention relates to the administration of drugs, specifically to a method of identifying the contents of a syringe.

2. Descriptions of Prior Art

Manufacturers of syringe-administered medications use several techniques to help medical professionals identify the contents of their vials. These techniques include color coded labels and somewhat standard arrangements of key information including generic name, trade name, expiration date and lot numbers. However, once these medications are transferred from a vial into a syringe, the techniques used to identify the medication in that syringe provide few positive controls and are subject to failure. The results of missed and unintended medication can range from unexpected susceptibility to disease to life-threatening and sometimes fatal incidents.

This problem is particularly acute in the pediatric office setting where numerous injections are given daily. Most children receive a minimum of 16 immunizations before the age of 18 months. That number is expected to increase in the next few years as new vaccines are approved for pediatric use. At least 12 of the immunizations presently given during this period are given via injections withdrawn from multi-dose vials. At some well child visits two and sometimes three injectable vaccines are given to one child using separate syringes and separate sites. Often there is a sibling who is also receiving immunizations at the same visit. It is not uncommon for a medical professional to prepare 4 or 5 syringes of vaccine from several vials at one time. In many medical practices the person preparing a syringe is not the person who will give the injection. In these situations, clearly communicating the contents of a syringe is crucial.

It is extremely difficult if not impossible to distinguish one vaccine from another once they have been withdrawn from their vials. They are usually given using the same type and size of syringe and most are given in a 0.5 cc dose. Moreover, several of the vaccines are identical in color and consistency.

Errors such as giving an incorrect medication or an incorrect dose can easily be made if the contents of the syringe cannot be positively identified from the point of time that the vaccine is withdrawn from its vial up to the moment of its administration.

For example, a child could inadvertently receive two doses of the same vaccine rather than the two separate vaccines ordered or, receive an incorrect vaccine, one meant for another child. A child receiving two different immunizations into two different sites could have a local reaction to one of them and there would be no way to distinguish which vaccine had caused the reaction. In a general practice where many different vials of medication are refrigerated together a child could receive a drug other than a vaccine or an adult could receive a vaccine meant for a child rather than the drug prescribed for them. Once the medication is withdrawn from its vial there is little opportunity to recheck its identity.

There is no universal method used to distinguish the contents of one syringe from another. Each medical practice has its own system for establishing and communicating the contents of a syringe. In some medical practices the medical professional preparing the injections is responsible for devising his or her own system. The following methods are commonly used to distinguish one injectable medication from another:

(a) identifying the content of the syringes based on the appearance of that content;

(b) arranging the syringes in a specific order and identifying them by remembering their locations;

(c) placing syringes on a medicine tray with an information card for each syringe;

(d) marking the syringes using stickers or permanent color marks;

(e) using a combination of the above methods.

All of the above methods can be unreliable. Visual identification of the medication is very difficult since several of the medications are identical or nearly identical in appearance. Memorization is not always reliable in medical settings where distractions include telephone and intercom calls, coworker's requests for assistance and emergency situations.

The organization of medicine trays with syringes and their corresponding information cards can be disturbed if the tray is tipped or moved abruptly.

Permanent marker on a syringe can be easily smudged by damp hands or hands that have just used an alcohol prep to clean the top of a vial. Information stickers have to be separately prepared and may not be readily available when the medication is being drawn or an incorrect sticker may be used.

If, in using the above methods, a medical professional becomes uncertain about the contents of a syringe, that syringe and its contents should be discarded. This is both wasteful and costly.

Although this discussion focuses on the use of injectable medications in the pediatric office, similar risks exist in hospital, nursing home, clinic and home care settings. Moreover, the problem is not limited to injectable medications. Ingestable medications such as pills present similar problems.

OBJECTS AND ADVANTAGES

The principle object of the present invention is to reduce errors in the administration of drugs and to improve the records kept of their use. These objects are accomplished as follows:

(a) placing a label dispenser on the medicine container provides a readily available and accurate source of labels for identifying syringes and maintaining medical records;

(b) the label can be attached to the syringe while the needle of the syringe is still inserted in the vial thus eliminating the possibility of applying an incorrect label;

(c) the contents of a syringe labeled in this manner may be verified at any time, up to and including the moment of injection. This can prevent both the administration of a medication drawn from the wrong vial and the administration of a correctly drawn medication to the wrong patient;

(d) when multiple medications are administered to a single patient, labeled syringes provide a more positive means of administering specific medications to predetermined sites and recording the sites used for each medication.

(e) the correspondence between the number of doses in a vial and the number of labels in the dispenser provides an indicator that the correct dosage is being used: if labels remain after the vial is empty then too large a dose may have been used, if a substantial amount of the vial contents remain after all labels have been used then too small a dose may have been used;

(f) label sequence numbers can make significant errors in dosage immediately apparent;

(g) the label can be easily removed from the syringe just prior to injection and used as a aid in maintaining patient or clinic records;

(h) the use of the label to maintain medical records saves time and improves the legibility and accuracy of these records;

OTHER OBJECTS AND ADVANTAGES (a) the label provides a reassuring identification to the patient, parent or guardian as to the type and amount of medication being given;

(b) the label dispenser does not interfere with normal vial handling or visual inspection of the vial contents;

(c) the positive identification of syringe contents afforded by this system avoids the expense of discarding medicine in syringes with contents that cannot be positively identified.

Further objects and advantages of our invention will be apparent from a consideration of the drawings and ensuing description.

DRAWING FIGURES

FIG. 11 illustrates the use of the syringe label as an aid in medical record keeping.

DESCRIPTION

FIGS. 1-8

Figure 1:
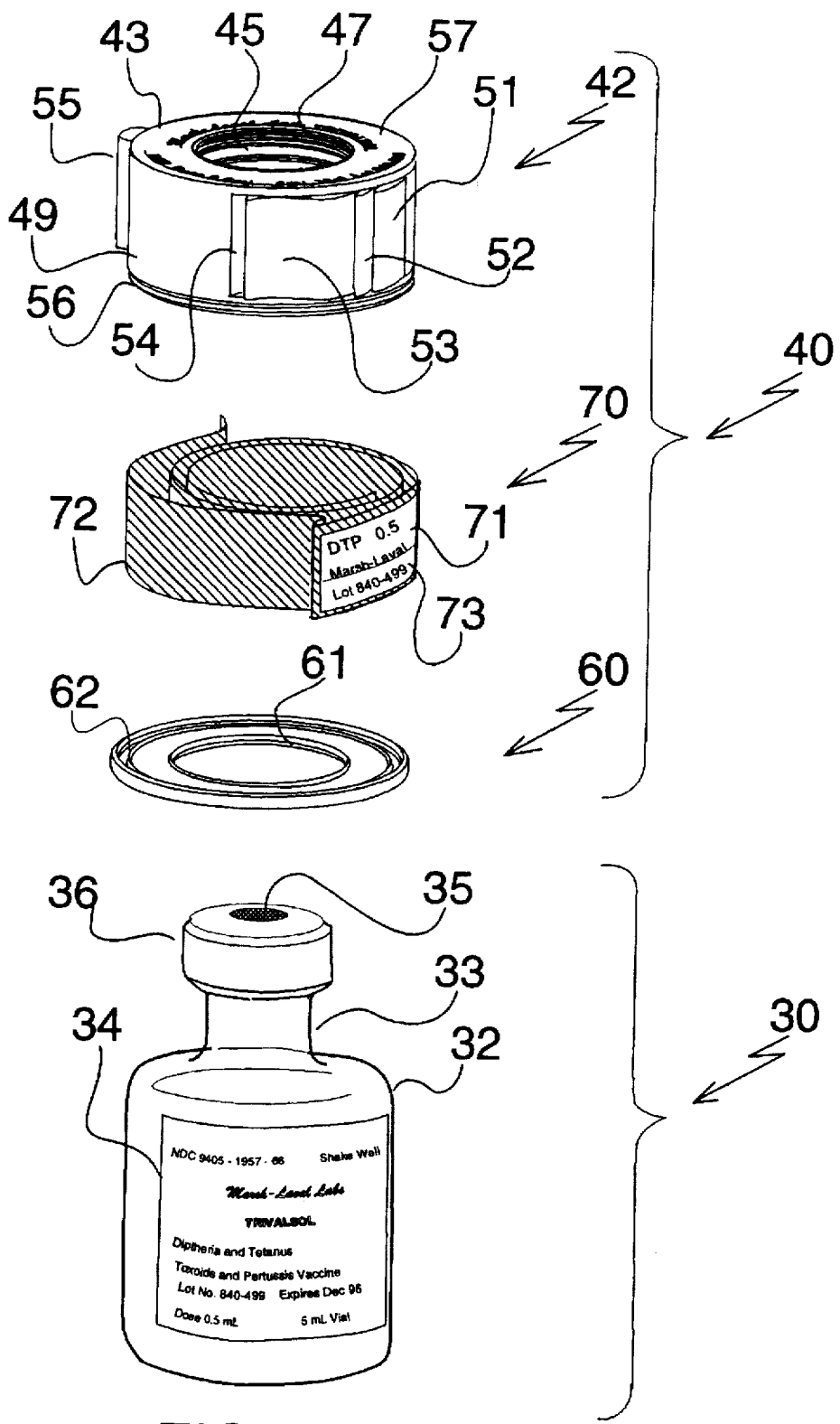
FIG. 1 is an exploded view showing a label dispenser, its component parts and indicating a manner of mounting a dispenser on a prior art medicine vial.

FIG. 1 illustrates an embodiment of a labeling device for use in our syringe content identification system. The device consists of a label dispenser 40 suitable for mounting on a prior art medicine vial 30.

Features of the prior art medicine vial are a vial seal 35 held on to a vial neck 33 by a vial cap 36. Information describing contents of the vial is printed on a label 34 mounted on a vial body 32.

The label dispenser consists of a dispenser body 42 a label tape 70 and a snap cover 60. A mounting hub 45 forms a hollow core in the dispenser body. The mounting hub's diameter is slightly larger than that of the vial cap. A dispenser label 57, identifying medication contained in the vial partially covers a dispenser top 43.

A dispensing mechanism forms an integral part of the outer wall 49 of the dispenser body and consists of a label tape guide 51, a delaminating edge 52, a carrier web return guide 53, and a carrier web exit slot 54. A discussion of the operation of this mechanism occurs in the discussion of FIG. 7. A carrier web 72 follows a feed path running from inside the dispenser body, across the delaminating edge, under the carrier web return guide and exits through the carrier web exit slot. The outer wall also includes a carrier web tear-off clamp 55.

Figure 6:
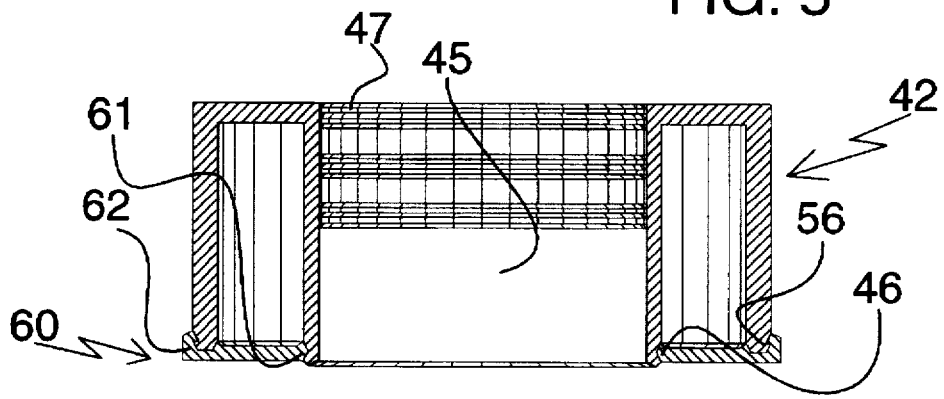
FIG. 6 is a front view, wire frame drawing of a vertical cross section of the label dispenser body with the snap cover attached.

The snap cover encloses the label tape in the dispenser body and stiffens the dispensing mechanism components. The snap cover attaches to the bottom of the outer wall using an outer snap ring 62 that fits tightly into an outer snap ring groove 56 molded into the dispenser body. An inner snap ring 61 tightly fits an inner snap ring groove 46 (FIG. 4) formed near the dispenser hub's lower outside edge. FIG. 6 illustrates the manner that the snap cover attaches to the dispenser body in greater detail.

A mounting ring set 47 molded into the hub's inner surface compress to secure the dispenser body to the vial.

Figure 2:
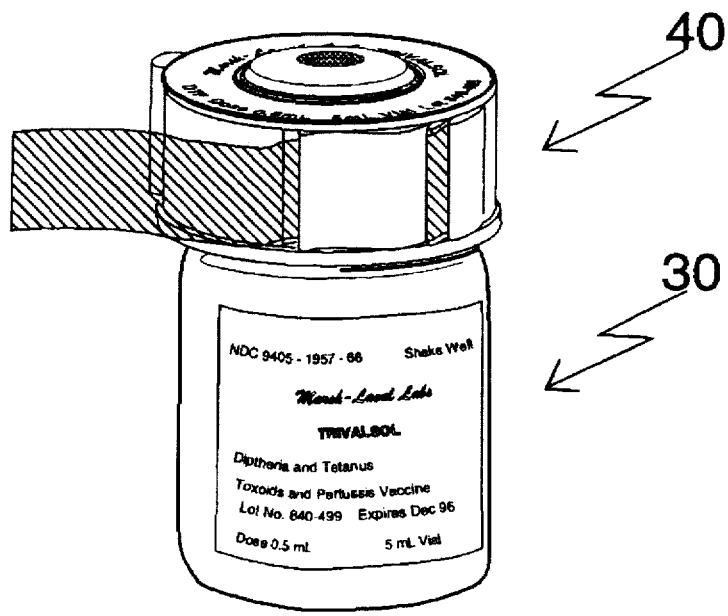
FIG. 2 illustrates a view of the assembled label dispenser mounted on the cap of a medicine vial.

FIG. 2 illustrates an assembled view of components shown in FIG. 1. This highly compact and ergonomic implementation minimizes interference between the labeling device and normal handling of the medicine vial.

Figure 3:
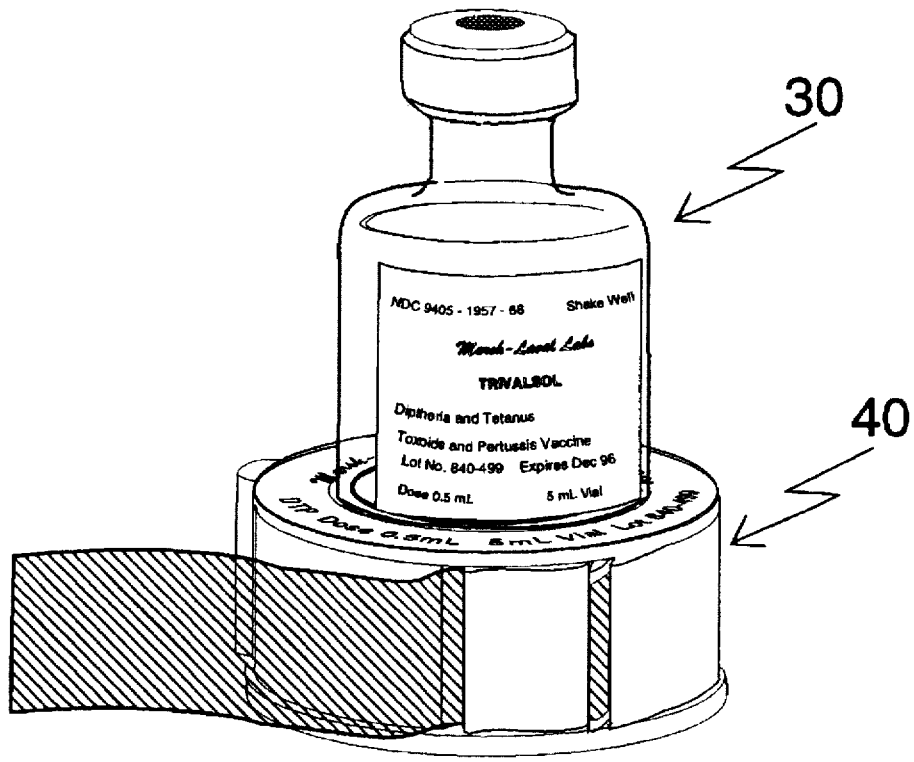
FIG. 3 illustrates the label dispenser mounted on the bottom of the vial body.

FIG. 3 illustrates mounting the label dispenser on the vial body. This alternative is less compact but allows the use of larger labels than a cap-mounted version.

Figure 4:
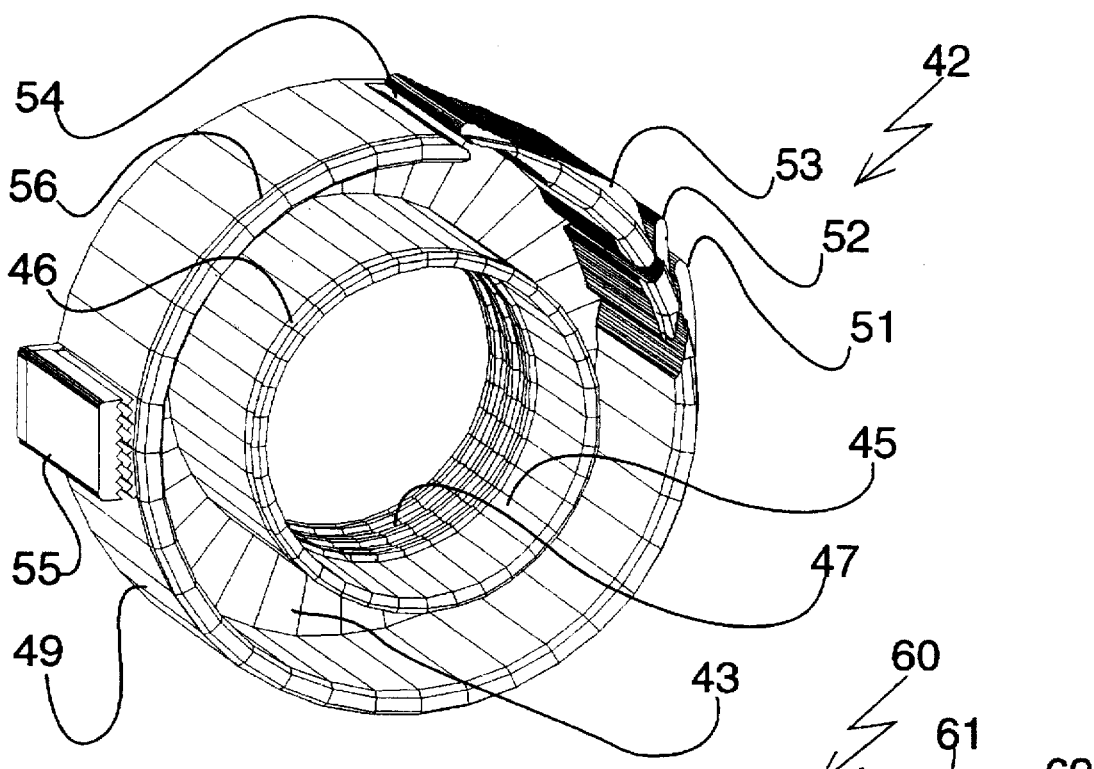
FIG. 4 is a perspective wire frame drawing of the dispenser body with hidden lines removed.
Figure 5:
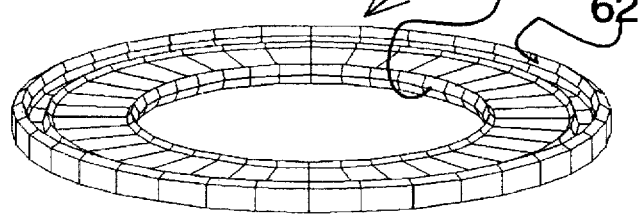
FIG. 5 is a perspective wire frame drawing of the snap cover with hidden lines removed.

FIGS. 4, 5 and 6 provide additional details on the dispenser body and the snap cover. FIGS. 4 and 6 show the inner snap ring groove and how it, along with the outer snap ring and outer snap ring groove, are used to attach the snap cover. FIG. 4 illustrates how the label tape guide, the delaminating edge, the label carrier return guide, and the label carrier exit slot extend from an intersection of the outer wall with the underside of the dispenser top to the outer wall bottom allowing the carrier web to be threaded from the dispenser body's bottom.

Figure 7:
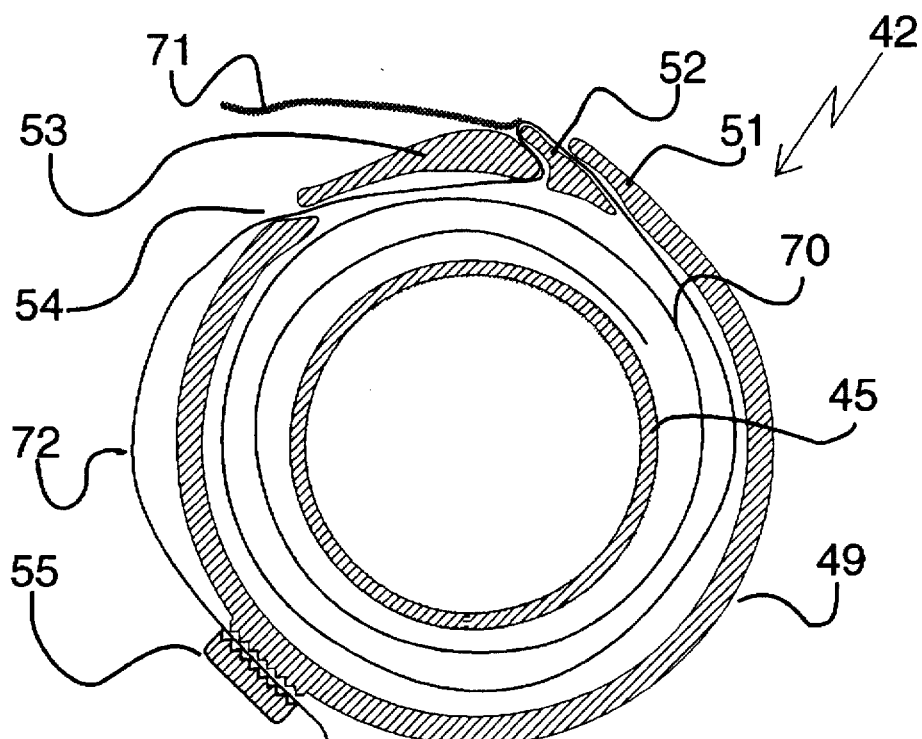
FIG. 7 is a vertical cross section of the label dispenser body showing the label dispensing mechanism and threading of the label tape.

FIG. 7 illustrates how the label tape threads through the dispensing mechanism. The syringe label 71 mounted on the carrier web that is stored inside the dispenser body. A leading end of the carrier web runs between the label tape guide and the delaminating edge. The label tape guide applies pressure to the label tape to create a drag required to hold the carrier web against the delaminating edge. The carrier web then winds around the delaminating edge and on to the carrier return guide forcing the carrier web to follow a small radius curve of the delaminating edge. A combination of the label's resistance to bending around this curve and the label's weak adhesion to the carrier web result in the syringe label breaking free of the carrier web. The carrier web then runs along the outer wall's inside surface and exits through the carrier web exit slot. Because feed path is open on the dispenser body's open end, the label tape can be directly loaded into the feed path rather than being threaded through it.

Figure 8:
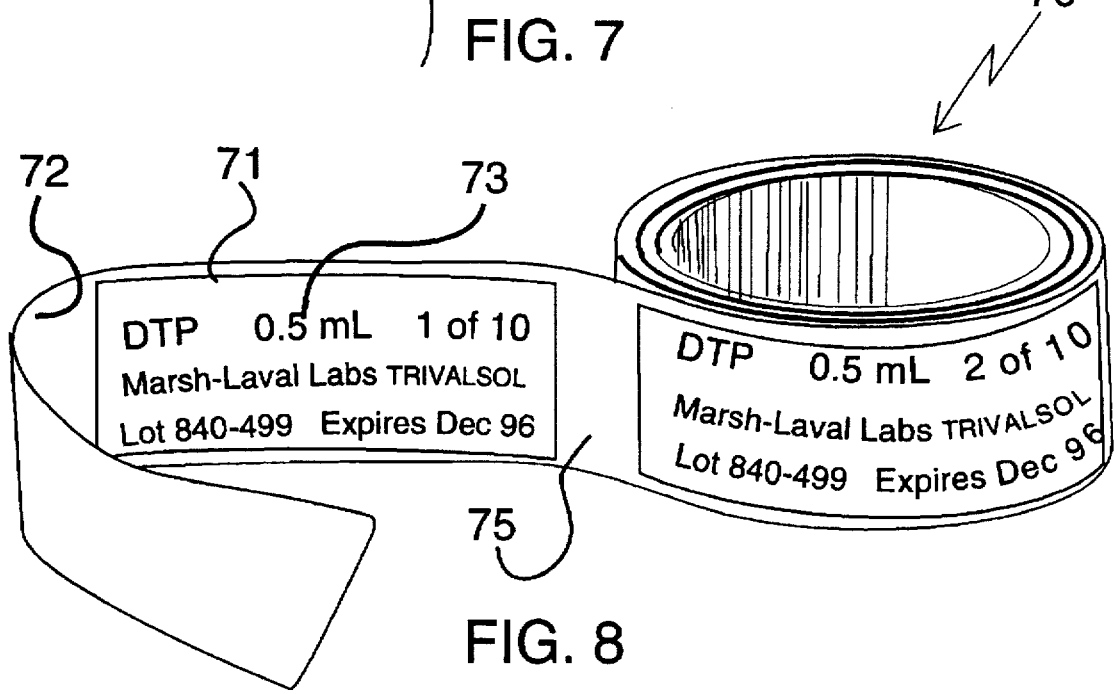
FIG. 8 is an illustration of the label tape used in the label dispenser.

FIG. 8 illustrates details of the label tape consisting of a number of the syringe labels on the carrier web. The carrier web is made of, or coated with, a material that prevents the syringe label from strongly adhering to it. A set of label information 73 is printed on each label. The information may include such items as generic medical name, dosage, label sequence, label id, manufacturer, trade name, lot number, and expiration date. The set of label information may be written in text or in computer readable coding or both. A gap 75 is maintained between labels to allow one label to be dispensed without exposing the subsequent syringe label.

Figures 9, 10:
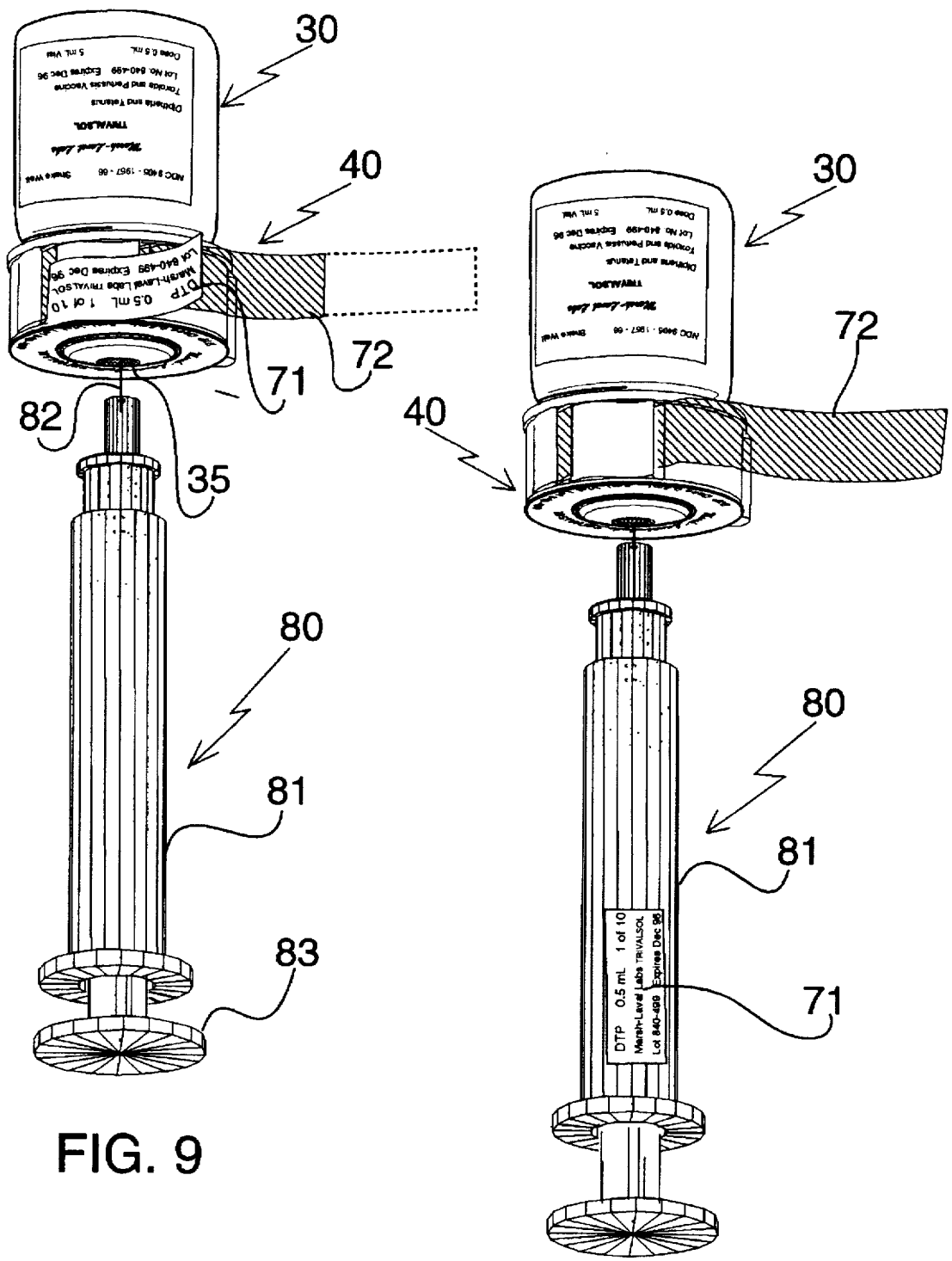
FIG. 9 and 10 are illustrations of the medication withdrawal and syringe labeling processes using this invention.

FIGS. 9, 10 and 11

When a medical professional draws an injectable vaccine from the vial, the correct labeling of the syringe and accurate records of an injection are facilitated by an integration of the label dispenser, correct syringe labels and the medicine vial.

As in prior art, a syringe needle 82 (FIG. 10) is inserted through the vial seal and into the vial. A prescribed amount of medicine is withdrawn from the vial by inverting the vial and pulling a syringe plunger 83 as necessary to draw a prescribed amount of medication into the syringe.

By holding the the vial and inserted syringe with one hand and pulling the exposed carrier web away from the carrier web exit slot (FIGS. 1, 4, 8) with the other, the carrier web is drawn, with the syringe label attached, out of the dispenser body, between the label tape guide and across the delaminating edge. As a leading edge of the syringe label encounters the small radius curve of the delaminating edge, its resistance to bending causes it to break free from the carrier web and move away from the dispenser body. When the trailing edge of the syringe label passes over the delaminating edge, it places the syringe label on an exterior side of the carrier web return guide. The medical professional removes the syringe label from the label dispenser and places it on a syringe body 81 (FIG. 10).

The excess length of the carrier web may be removed by inserting the carrier web in the tear-off clamp, pressing the clamp to close it against its opposing ridges on the outer wall and tearing off the web using an edge of the clamp furthest from the exit slot.

At the time of an injection the syringe label is rechecked and may then be removed for use in maintaining an accurate record of the injection (FIG. 11).

Construction

Both the dispenser body and the snap cover are molded from a plastic material such as polyethyleneterepfthalate (PET). Approximate thicknesses of the dispenser body are: outer wall, 1 mm; the dispenser top, 0.8 mm; the hub, 0.6 mm. Approximate dimensions of the dispenser body are: diameter, 23 mm; height, 10.6 mm; the hub inside diameter, 13 mm. The snap cover is approximately 0.6 mm thick and 24 mm in diameter. These measurements are approximate and will vary depending on such things as the vial and the cap dimensions and the syringe label quantity, thickness and length.

Reference Numerals in Drawings The items referenced in the drawings are listed below with their reference numbers and indented to reflect their hierarchical organization.

30. Medicine vial comprising:
  32. Vial body
  33. Vial neck
  34. Vial label
  35. Vial seal
  36. Vial cap
40. Label Dispenser comprising:
  42. Dispenser body comprising
  43. Dispenser top
  45. Mounting hub comprising:
    46. Inner snap ring groove
    47. Mounting ring set
  49 Outer wall
  50 Dispensing mechanism comprising:
    51. Label tape guide
    52. Delaminating edge
    53. Carrier web return guide
    54. Carrier web exit slot
    55. Carrier web tear off clamp
    56. Outer snap ring groove
    57. Dispenser label
  60. Snap cover
    61. Inner snap ring
    62. Outer snap ring
  70. Label tape comprising:
    71. Syringe label
    72. Carrier web
    73. Label information
    75. Inter-label gap
80. Syringe comprising:
  81. Syringe Body
  82. Syringe Needle
  83. Syringe Plunger

Summary, Ramifications and Scope

Thus the reader will see that the Syringe Content Identification System is a highly effective and inexpensive method of ensuring that prescribed medications are appropriately administered to an intended patient, and that accurate and complete records of these injections are maintained. In addition, many patients, parents and guardians will find the presence of the identifying label on the syringe reassuring. And finally, the correspondence between a number of labels in a dispenser and a number of doses in a vial provides a positive method for flagging several, potentially life threatening, procedural errors that would otherwise go undetected.

While the above description contains many specificities these should not be construed as limitations on the scope of the invention but rather as an exemplification of preferred embodiments thereof. Many other variations are possible. For example:

1. The mounting rings could be replaced by bonding the mounting hub directly to the vial cap or vial body using adhesive or other bonding means.

2. The label dispenser body designed to be mounted around the vial cap can be simplified by bonding the bottom of the outer wall directly to the vial body making the snap cover, the mounting hub, and the mounting rings unnecessary;

3. The dispenser body and the vial body could be formed as a single unit.

4. Multiple labels per dose could be issued providing a separate label for such things as a patient's personal vaccination record. This could be achieved by either issuing several single labels per dose or by using multi layered labels.

5. Although the discussion and drawings focus on injectable medications, syringes and vials, this system can be applied to identify and record the use of ingestable medications as well. The label could be applied to a medicine cup to identify its contents and subsequently used to record the taking of the medication in the patient record. In situations where the patient is responsible for the administration of his own medications, the label can be used with a personal calendar to maintain a clear record of that administration in a format that could easily be reviewed by a medical professional.

6. The benefit of using these processes and devices is extensible beyond their medical application. For example, this system can be directly applied to manufacturing processes where substances are transported outside their original containers and where positive identification of these substances at the point of application, and accurate recording of their use, is crucial.

We claim:

1. A method of identifying a substance after said substance is removed from a container comprising the steps of:
   (a) providing a label dispenser having means for integration with said container and means for dispensing a strip of multiple labels with each label corresponding to each issue of said substance from said container, said strip of labels is freely received within said label dispenser for sequentially removal, each said label presenting sufficient information for identifying said substance (b) periodically withdrawing a quantity of said substance from said container, and withdrawing one of said plurality of labels when said substance is withdrawn (c) attaching said label to a vessel to which the said substance is transferred concurrently with the transfer thereby enabling a determination to be made at the site of an application of said substance that said substance conveyed by said vessel is appropriate for said application.

2. The method of claim 1 wherein said label is removed from said vessel concurrently with the application of said substance and subsequently used to establish a permanent record of said application.

3. The method of claim 1 wherein said container is a medicine vial and said substance is a medicine contained in said vial and said vessel is a syringe and said application is an injection of said medicine into a patient and said information is selected from the group consisting of generic medication name and dosage and label sequence and manufacturer name and medicine trade name and lot number and expiration date.

4. The method of claim 3 wherein concurrently with said injection said label is removed from said syringe and used to establish a permanent record of said injection.

5. The method of claim 1 wherein said container is a medicine bottle and the substance is an ingestable medication and said vessel is a medicine cup and said application is the ingestion of the medicine by a patient and said information is selected from the group medication name and dosage and label sequence and manufacturer name and medicine trade name and lot number and expiration date.

6. The method of claim 5 wherein concurrently with said ingestion said label is removed from said medicine cup and used to establish a permanent record of said ingestion.

7. A label dispenser, integrated with a container, for supplying adhesive labels, said labels reciting attributes of a substance contained in said container comprising:
   (a) a strip of multiple adhesive labels with attributes of said substance printed thereon,
   (b) a dispenser body for enclosing unexpended portion of said strip,
   (c) dispensing means for successively providing said labels, and
   (d) integrating means for combining said label dispenser with said container
   (e) said integrating means comprising a center located circular mounting ring set to secure said dispenser on said container whereby a positive correlation is maintained between said substance in said container and said attributes printed on said labels provided by said dispensing means.

8. The label dispenser of claim 7 wherein said dispensing means includes:
   (a) a carrier web on which said labels are releaseably mounted,
   (b) a delaminating edge having a curve with a radius sufficiently small to cause said labels to break free from said carrier web when said carrier web is slidingly moved around said curve, and
   (c) a feed path leading from inside said dispenser body around said delaminating edge and under a carrier web return guide whereby pulling an exposed length of said carrier web away from said dispenser body moves said carrier web with said labels attached to said delaminating edge where a resistance of said labels to bending around said curve causes said labels to delaminate from said carrier web and come to rest on an exterior surface of said dispenser body.

9. A label dispenser, integrated with a container, for supplying adhesive labels, said labels reciting attributes of a substance contained in said container comprising:
   (a) a strip of adhesive labels with attributes of said substance printed thereon,
   (b) a dispenser body for enclosing unexpended portion of said strip,
   (c) dispensing means for successively providing said labels, and
   (d) integrating means for combining said label dispenser with said container,
   (e) said integrating means comprising a center located circular mounting ring which uses adhesive bonding means to secure said dispenser on said container.

10. A label dispenser, integrated with a container, for supplying adhesive labels, said labels reciting attributes of a substance contained in said container comprising:
   (a) a strip of adhesive labels with attributes of said substance printed thereon,
   (b) a dispenser body for enclosing unexpended portion of said strip,
   (c) dispensing means for successively providing said labels, and
   (d) integrating means for combining said label dispenser with said container,
   (e) said integrating means includes molding said dispenser body as part of said container.

* * * * *